United States Patent [19]

Okawa et al.

[11] Patent Number: 5,395,955
[45] Date of Patent: Mar. 7, 1995

[54] METHOD FOR THE PREPARATION OF CARBINOL GROUP-CONTAINING ORGANOPOLYSILOXANE

[75] Inventors: Tadashi Okawa; Ryuzo Mikami, both of Ichihara, Japan

[73] Assignee: Dow Corning Toray Silicone Company, Ltd., Tokyo, Japan

[21] Appl. No.: 737,523

[22] Filed: Jul. 29, 1991

[30] Foreign Application Priority Data

Jul. 30, 1990 [JP] Japan ................................ 2-202193

[51] Int. Cl.⁶ ............................ C07F 7/08; C07F 7/18
[52] U.S. Cl. ........................................................ 556/449
[58] Field of Search .......................................... 556/449

[56] References Cited

U.S. PATENT DOCUMENTS

| | | | |
|---|---|---|---|
| 2,629,727 | 2/1953 | Speier | 556/449 |
| 2,924,588 | 2/1960 | Speier | 556/449 X |
| 3,442,925 | 5/1969 | Sinuler et al. | 556/449 |
| 4,375,548 | 3/1983 | Wang et al. | 556/449 X |
| 5,113,005 | 5/1992 | Celebriski | 556/449 |

*Primary Examiner*—Paul F. Shaver
*Attorney, Agent, or Firm*—George A. Grindahl

[57] ABSTRACT

This invention provides method for the preparation of carbinol-modified organopolysiloxane which does not suffer from the secondary reaction problems of the art and which thereby makes possible the production of high-purity carbinol-containing organopolysiloxane.

The method involves a platinum-catalyzed addition reaction of an organopolysiloxane having at least 1 silicon-bonded hydrogen atom in each molecule and an organic compound whose molecule contains at least 1 aliphatically unsaturated hydrocarbon group and at least 1 triorganosilyl-blocked carbinol group. Thereafter a desilylation reaction on the organopolysiloxane product is accomplished in an essentially water-free mixture of organic carboxylic acid and alcohol to provide carbinol-modified organopolysiloxane.

1 Claim, No Drawings

METHOD FOR THE PREPARATION OF CARBINOL GROUP-CONTAINING ORGANOPOLYSILOXANE

BACKGROUND OF THE INVENTION

1. Technical Field

The present invention relates to a method for the preparation of carbinol group-containing organopolysiloxane.

2. Prior Art

Several methods have been proposed for the preparation of carbinol group-containing organopolysiloxane. For example, Japanese Patent Application Laid Open [Kokai or Unexamined] Number 60-206834 [206,834/85] teaches a method for the preparation of carbinol-containing organopolysiloxane which proceeds as follows: an addition reaction is first run between trimethylsilyl-blocked allyl alcohol and SiH-containing organopolysiloxane, and this is followed by a desilylation reaction using aqueous hydrochloric acid. The corresponding reaction equations are provided below (Me=methyl).

addition reaction

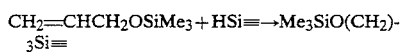

desilylation reaction

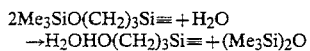

PROBLEMS TO BE SOLVED BY THE PRESENT INVENTION

However, side reactions inevitably occur during the execution of the aforesaid method because the desilylation reaction is run in a water-containing reaction system (aqueous hydrochloric acid, etc.). This greatly complicates the recovery of high-purity carbinol-containing organopolysiloxane. Thus, siloxane bond cleavage reactions occur during the execution of the desilylation reaction under consideration. For example, when the disiloxane

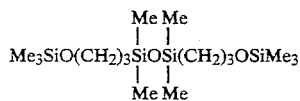

is desilylated in aqueous hydrochloric acid, the main reaction product is (I), but a secondary reaction product (II) is also produced due to cleavage of the disiloxane.

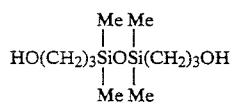   (I)

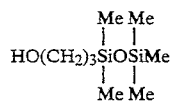   (II)

Moreover, when this method is used to synthesize carbinol-containing organopolysiloxane with molecular weights above several hundred, siloxane bond scission occurs due to secondary reactions, as illustrated by the reaction equation given below, and this leads to the appearance of the silanol group at the molecular chain terminal. Low-molecular-weight carbinol-containing organopolysiloxane is concurrently produced, but it distills from the reaction system together with other low boilers which have been produced. As a consequence, the carbinol content in the obtained carbinol-containing organopolysiloxane will be below the calculated value.

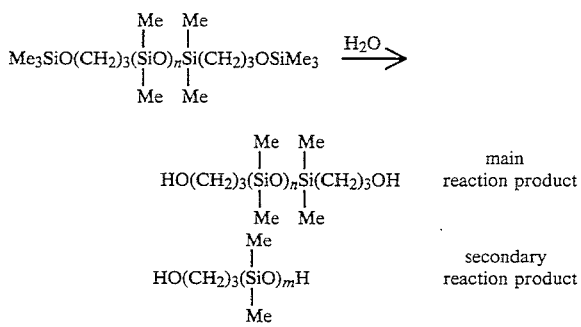

These secondary reactions make it very difficult to obtain high-purity carbinol-containing organopolysiloxane with the desired molecular structure.

The present invention takes as its object the introduction of a method for the preparation of carbinol-modified organopolysiloxane which does not suffer from the aforementioned problems and which thereby makes possible the production of high-purity carbinol-containing organopolysiloxane.

DETAILED DESCRIPTION OF THE INVENTION

The present invention relates to a 1. method for the preparation of carbinol group-containing organopolysiloxane, wherein said method is characterized by the preparation of organopolysiloxane that contains the triorganosilyl-blocked carbinol group by an addition reaction, in the presence of platinum-type catalyst, between organopolysiloxane having at least 1 silicon-bonded hydrogen atom in each molecule and an organic compound whose molecule contains at least 1 aliphatically unsaturated hydrocarbon group and at least 1 triorganosilyl-blocked carbinol group, followed by the execution of a desilylation reaction on the organopolysiloxane product in an essentially water-free mixture of organic carboxylic acid and alcohol.

To explain the preceding in greater detail, one of the starting materials employed by the present invention takes the form of an organic compound whose molecule contains at least 1 aliphatically unsaturated hydrocarbon group and at least 1 triorganosilyl-blocked carbinol group. Such organic compounds are in fact known, for example, as disclosed in Japanese Patent Application Laid Open Number 60-206834 [206,834/85]. These compounds are obtained by the silylation with a silylating agent of an alcohol whose molecule contains at least 1 aliphatically unsaturated hydrocarbon group and at least 1 carbinol group. The alcohols under consideration are exemplified by allyl alcohol, methacryl alcohol, ethylene glycol monoallyl ether, glycerol monoallyl ether, trimethylolpropane monoallyl ether, trimethylolethane monoallyl ether, pentaerythritol monoallyl ether, and so forth. Said silylating agent is exemplified by trimethylchlorosilane, hexamethyldisilazane, and so forth.

Like the above-described organic compound, the organopolysiloxane having at least one SiH in each molecule which is used by the present invention is a starting material for the present invention. This organopolysiloxane is exemplified by organopolysiloxanes with the following general formulas.

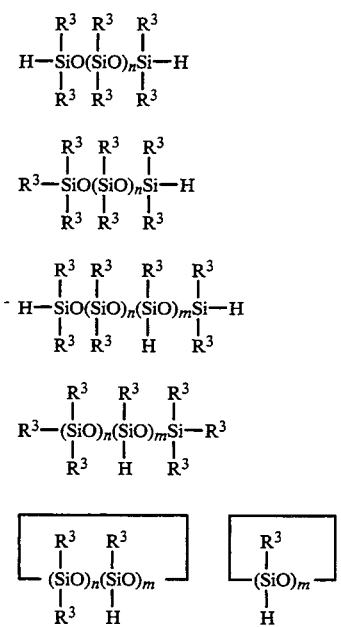

(In the preceding formulas, $R^3$=monovalent organic groups as exemplified by alkyl groups such as methyl, ethyl, propyl, and butyl; aryl groups such as phenyl, tolyl, and xylyl; aralkyl groups such as benzyl and phenethyl; and halogenated hydrocarbon groups such as chloromethyl and 1,1,1-trifluoropropyl; and n and m are positive integers.)

While the molecular weight of this organopolysiloxane is not specifically restricted, values of 144 to 100,000 are preferred and values of 144 to 10,000 are even more preferred.

Within the context of the present invention, triorganosilyl-blocked carbinol-containing organopolysiloxane is first prepared by an addition reaction, in the presence of platinum-type catalyst, between the above-described organopolysiloxane having at least 1 SiH in each molecule and the above-described organic compound whose molecule contains at least 1 aliphatically unsaturated hydrocarbon group and at least 1 triorganosilyl-blocked carbinol group. The platinum-type catalyst employed here is exemplified by chloroplatinic acid, platinum/olefin complexes, complexes between chloroplatinic acid and vinylsiloxane, and so forth. This addition reaction is preferably conducted under conditions such that the number of moles of triorganosilyl-blocked carbinol group in the organic compound is somewhat larger than the number of moles of silicon-bonded hydrogen atoms in the polysiloxane. After the addition reaction, the excess organic compound can be easily eliminated by, for example, distillation. While this addition reaction can be run at from room temperature to 150 degrees Centigrade, it is preferably run within the range of 60 to 150 degrees Centigrade in order to shorten the reaction time. Furthermore, this addition reaction may be run using an organic solvent, and optimal in this respect are aromatic hydrocarbons such as benzene, toluene, xylene, etc., and ethers such as diethyl ether, tetrahydrofuran, etc.

The resulting organopolysiloxane carrying triorganosilyl-blocked carbinol is then desilylated in an organic carboxylic acid plus alcohol mixture. This mixture of organic carboxylic acid and alcohol must be essentially free of water. When water is present in this mixture, the above-described secondary reactions occur during the desilylation reaction, and it then becomes impossible to obtain the target carbinol-containing polysiloxane at high purities. The organic carboxylic acid used here is exemplified by acetic acid, propionic acid, and so forth. The alcohol is exemplified by methanol, ethanol, and so forth.

The desilylation reaction will not proceed to completion when too little organic carboxylic acid is used, while secondary reactions develop when too much is used. Either case results in a reduction in the purity of the target carbinol-containing organopolysiloxane. Accordingly, the preferred use range for the organic carboxylic acid is 10 to 10,000 weight parts per 1,000,000 weight parts triorganosilyl-blocked carbinol-containing organopolysiloxane. The particularly preferred range is 100 to 90,000 weight parts per 1,000,000 weight parts triorganosilyl-blocked carbinol-containing organopolysiloxane. The alcohol is preferably used in a quantity at least roughly equal to that of the triorganosilyl-blocked carbinol-containing organopolysiloxane. This desilylation reaction will proceed even at room temperature, but its execution at higher temperatures is preferred in order to raise the reaction rate. In concrete terms, the reaction is preferably run by reaction at the boiling point of the alcohol while removing the by-produced triorganomonoalkoxysilane from the reaction system. The organic solvent as discussed above in connection with the addition reaction can also be used in this desilylation reaction.

In the prior methods in which the desilylation reaction was conducted in a water-containing reaction system, multiple water washes were required after completion of the reaction in order to remove residual acid or alkali component. However, this water-washing step can be omitted from the preparative method according to the present invention, and this makes possible an even more efficient preparation of the target carbinol-modified polysiloxane.

EXAMPLES

The present invention is explained below in greater detail through illustrative examples. In the examples, parts=weight parts, Me=methyl, and Bu=butyl.

EXAMPLE 1

33.6 Parts tetramethyldisiloxane and 65.1 parts organic compound with the formula $CH_2=CHCH_2-OSiMe_3$ were introduced with mixing to homogeneity into a 200 mL three-neck flask equipped with a stirrer, thermometer, and reflux condenser. This was followed by the introduction with mixing of 0.4 parts isopropanolic chloroplatinic acid solution (chloroplatinic acid content=0.4 weight %). At this point, the temperature in the flask rose to 50 degrees Centigrade. The temperature was raised further to 70 degrees Centigrade in order to run the reaction. The reaction was monitored by gas chromatography: it was terminated when the peak for the starting tetramethyldisiloxane had disappeared. The low boilers were distilled off in vacuo, and a fraction boiling at 139 degrees Centigrade/4 mmHg was collected. This fraction was analyzed by proton nuclear magnetic resonance (NMR) and was determined to be a disiloxane compound with the following chemical structure.

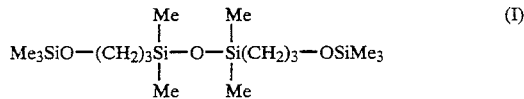

50 Parts disiloxane (I), 400 parts methanol, and 0.01 part acetic acid were introduced into a 1,000 mL three-neck flask equipped with a stirrer, thermometer, and reflux condenser, and the temperature was raised to the reflux temperature. A desilylation reaction was run under reflux while removing the Me₃SiOMe by-product from the reaction system. After completion of the reaction, the low boilers were distilled off in vacuo at 60 degrees Centigrade to afford 31.3 parts carbinol-containing disiloxane. The actual carbinol group content in this carbinol-containing disiloxane was 13.5 weight %, and this value was in excellent agreement with the theoretical value of 13.6 weight %. The results from proton and $^{29}$Si NMR analyses demonstrated that the obtained carbinol-containing disiloxane was a compound with the following chemical structure (purity=100%).

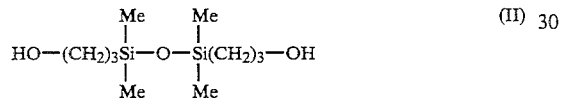

EXAMPLE 2

Polysiloxane with the average structural formula

and containing 0.0561 weight % silicon-bonded hydrogen and 0.13 parts of a 1 weight % solution of chloroplatinic acid in tetrahydrofuran were placed in a 500 mL four-neck flask equipped with stirrer, addition funnel, thermometer, and reflux condenser, and the temperature was gradually raised to 60 degrees Centigrade. 21.8 Parts of an organic compound with the formula CH₂=CHCH₂—OSiMe₃ was then added dropwise from the addition funnel, and the temperature in the flask rose to 77 degrees Centigrade due to the exothermic reaction. The reaction was continued at 60 to 70 degrees Centigrade for 3 hours. After it had been confirmed that the absorption characteristic of silicon-bonded hydrogen was absent from the infrared absorption spectrum, the low boilers were distilled off in vacuo to afford 266.9 parts of a transparent liquid polysiloxane. The obtained siloxane had the following structure according to the results of proton and $^{29}$Si NMR analyses.

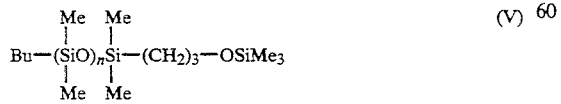

20 Parts polydimethylsiloxane (V) thus obtained, 20 parts methanol, and 0.176 parts acetic acid were then introduced into a 100 mL three-neck flask equipped with stirrer, thermometer, and reflux condenser, and the temperature was raised to the reflux temperature. The desilylation reaction was conducted under reflux while distilling the Me₃SiOMe product from the system. After the reaction, the low boilers were removed by distillation in vacuo at 60 degrees Centigrade to give 19.1 parts carbinol-containing polydimethylsiloxane. Its actual carbinol content of 9.1 weight % was in excellent agreement with the theoretical value of 9.2 weight %. The results from $^{29}$Si NMR analysis are reported in the following table. Based on these results, it was found that no silanol group had been produced by secondary reactions and that the desired carbinol-containing polydimethylsiloxane (VI) with the following structure had been obtained.

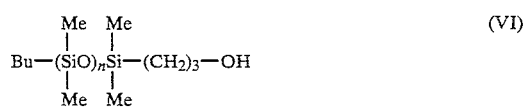

| Results of $^{29}$Si NMR Analysis for Polysiloxane (VI) | |
|---|---|
| structure | molar ratio (%) |
| HO(CH₂)₃Si(Me)(Me)—O— | 8.3 |
| —OSi(Me)(Me)—O— | 91.7 |
| —OSi(Me)(Me)—OH | 0 |

EXAMPLE 3

178 Parts of an organic compound with the formula

CH₂=C(Me)—CH₂—OSiMe₃ was introduced into a 1,000 mL four-neck flask equipped with a stirrer, thermometer, reflux condenser, and addition funnel. The temperature was gradually raised to 50 degrees Centigrade, and 1.1 parts of a 1 weight %
solution of chloroplatinic acid in tetrahydrofuran was introduced. 373 Parts polydimethylsiloxane with the average structural formula

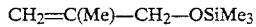

and containing 0.3013 weight % silicon-bonded hydrogen was added dropwise from the addition funnel over 30 minutes. The temperature in the flask had risen to 110 degrees Centigrade at the completion of addition due to the exothermic reaction. The temperature was then raised to 120 degrees Centigrade and a reaction was carried out at this temperature for 2 hours. Samples were taken, and the low boilers were distilled off in vacuo when it could be confirmed that the absorption characteristic of SiH was no longer present in the infrared absorption spectrum. The product was 536 parts polysiloxane (VII) with the following structure.

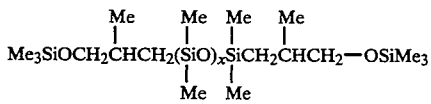

20 Parts polysiloxane (VII), 20 parts methanol, and 1.76 parts acetic acid were introduced into a 100 mL three-neck flask equipped with stirrer, thermometer, and reflux condenser, and the temperature was raised to the reflux temperature. The desilylation reaction was run under reflux while distilling the Me₃SiOMe product from the system. After the reaction, the low boilers were distilled off in vacuo at 60 degrees Centigrade to give 16.5 parts carbinol-containing polydimethylsiloxane (VIII) with the following structure.

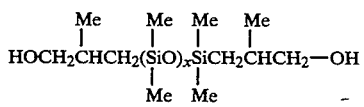

Its actual carbinol content of 4.20 weight % was in excellent agreement with the theoretical value of 4.:21 weight %. In addition, the results of ²⁹Si NMR analysis indicated that no silanol groups were present and thus that the desired polysiloxane (VII) had been obtained at high purity.

EXAMPLE 4

130 Parts organic compound with the formula

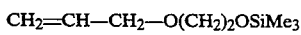

and 100 parts polysiloxane with the average structural formula $Me_3SiO(Me_2SiO)_6(MeHSiO)_7SiMe_3$ and having 0.68 weight % SiH were introduced into a 500 mL four-neck flask equipped with stirrer, thermometer, and reflux condenser, and the temperature was gradually raised to 70 degrees Centigrade. 0.1 Part of a 1 weight % solution of chloroplatinic acid in tetrahydrofuran was then introduced. An exothermic reaction immediately developed and the temperature in the flask rose to 95 degrees Centigrade. The temperature was subsequently raised to 100 degrees Centigrade and a reaction was run for 2 hours at this temperature. Samples were taken, and the low boilers were distilled off in vacuo when it could be confined that the absorption characteristic of SiH was no longer present in the infrared absorption spectrum. 250 Parts methanol and 1.9 parts acetic acid were then introduced into the flask, and the temperature was raised to the reflux temperature. The desilylation reaction was run under reflux while distilling the Me₃SiOMe product from the system. After the reaction, the low boilers were distilled off in vacuo at 60 degrees Centigrade to give 165 parts carbinol-containing polydimethylsiloxane (IX) with the following structure.

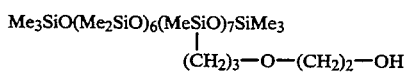

Its actual carbinol content of 6.83 weight % was in excellent agreement with the theoretical value of 6.84 weight %. In addition, the results of ²⁹Si NMR analysis indicated that no silanol groups were present and thus that the desired polysiloxane (IX) had been obtained at high purity.

Comparison Example 1

39.5 Parts of the siloxane compound (I) obtained in Example 1 was placed in a 100 mL three-neck flask equipped with stirrer, thermometer, and reflux condenser. 1.8 Parts 0.1N aqueous hydrochloric acid was introduced and a desilylation reaction was run for 4 hours at room temperature. After the reaction, the reaction mixture was dissolved in ether and this was washed 5 times with water. The solvent and low boilers were removed by distillation to afford a carbinol-containing siloxane compound. Analysis of the desilylation product by proton and ²⁹Si NMR analyses confirmed it to be a mixture of the two species given below. The desired dicarbinol-modified disiloxane was obtained only at 30%, while the major fraction was the monocarbinol-containing disiloxane produced by secondary reactions.

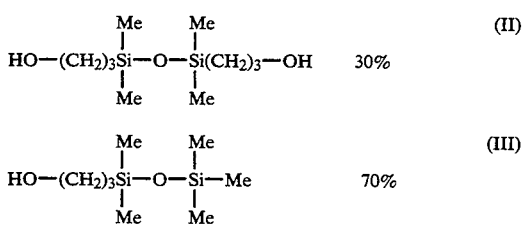

Comparison Example 2

147 Parts of an organic compound with the formula

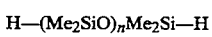

was introduced into a 1,000 mL four-neck flask equipped with a stirrer, thermometer, reflux condenser, and addition funnel. The temperature was gradually raised to 90 degrees Centigrade, and 1.1 parts of a 1 weight % solution of chloroplatinic acid in tetrahydrofuran was introduced. 403 Parts polydimethylsiloxane with the average structural formula $H—(Me_2SiO)_nMe_2Si—H$ and containing 0.2302 weight % silicon-bonded hydrogen was added dropwise from the addition funnel over 30 minutes. The temperature in the flask had risen to 105 degrees Centigrade at the completion of addition due to the exothermic reaction. The temperature was then raised to 120 degrees Centigrade and a reaction was carried out at this temperature for 1 hour. Samples were taken, and the low boilers were distilled off in vacuo when it could be confirmed that the absorption characteristic of SiH was no longer present in the infrared absorption spectrum. The results of proton and ²⁹Si NMR analyses confirmed the obtained polysiloxane to be a polydimethylsiloxane with the following chemical structure.

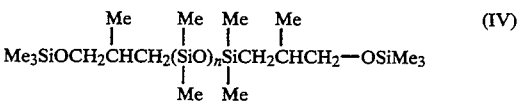

537 Parts polydimethysiloxane compound (IV) was introduced into a 1,000 mL three-neck flask equipped with stirrer, thermometer, and reflux condenser, and the temperature was gradually raised to 30 degrees Centigrade with stirring. 54 Parts 0.7N aqueous hydrochloric acid was added and a reaction was run at this temperature for 2 hours. After the desilylation reaction, the reaction mixture was dissolved in 500 parts toluene and this toluene solution was washed with water. The low boilers (e.g., toluene) were distilled off in vacuo to give a carbinol-modified polydimethylsiloxane. The actual carbinol content as determined by acetylation/titration was 2.39 weight %, which was smaller than the theoretical carbinol content of 3.35 weight %. In order to determine the cause of this, the carbinol-modified polydimethylsiloxane was analyzed by $^{29}$Si NMR, and the obtained results are reported in the following table. These results confirmed that the carbinol-modified polydimethylsiloxane contained silanol groups which are believed to originate in secondary reactions. As a consequence of such secondary reactions occurring in the desilylation reaction using aqueous hydrochloric acid, the desired carbinol-modified polydimethylsiloxane could not be obtained in high purity.

| Results of $^{29}$Si NMR Analysis for Polysiloxane of Comparison Example 2 | |
|---|---|
| structure | molar ratio (%) |
| HOCH$_2$CHCH$_2$Si(Me)(Me)—O— | 14.5 |
| —OSi(Me)(Me)—O— | 82.9 |
| HOSi(Me)(Me)—O— | 2.6 |

Comparison Example 3

260 Parts polydimethylsiloxane (V) as obtained in Example 2 and 360 parts methanol were introduced into a 1,000 mL three-neck flask equipped with stirrer, thermometer, and reflux condenser. The temperature was raised to the reflux temperature and a reaction was run for 3 hours at this temperature. The low boilers (methanol, etc.) were distilled off in vacuo after the reaction. The carbinol content in the obtained polysiloxane was 0.21 weight %, which was lower than the theoretical value of 0.92 weight %. The results of $^{29}$Si NMR analysis indicated that desilylation had not proceeded to completion, and in fact the majority of the carbinol groups had remained unaltered and blocked by the trimethylsilyl group. Thus, the desilylation reaction could not be run to completion using only methanol, and the desired carbinol-modified polydimethylsiloxane could not be obtained in high purity.

EFFECTS OF THE INVENTION

In the present invention's method for the preparation of organopolysiloxane, organopolysiloxane carrying triorganosilyl-blocked carbinol is first prepared by an addition reaction, in the presence of a platinum-type catalyst, between organopolysiloxane having at least 1 SiH in each molecule and an organic compound whose molecule contains at least 1 aliphatically unsaturated hydrocarbon group and at least 1 triorganosilyl-blocked carbinol. The organopolysiloxane product is then subjected to a desilylation reaction in an essentially water-free mixture of organic carboxylic acid and alcohol. This preparative method is characterized by freedom from secondary reactions and the ability to give carbinol-containing organopolysiloxane in high purities.

That which is claimed is:

1. Method for the preparation of a carbinol group-containing organopolysiloxane, wherein said method is characterized by the preparation of an organopolysiloxane that contains the triorganosilyl-blocked carbinol group by an addition reaction, in the presence of platinum-type catalyst, between an organopolysiloxane having at least 1 silicon-bonded hydrogen atom in each molecule and an organic compound whose molecule contains at least 1 aliphatically unsaturated hydrocarbon group and at least 1 triorganosilyl-blocked carbinol group, followed by the execution of a desilylation reaction on the organopolysiloxane product in an essentially water-free mixture of organic carboxylic acid and alcohol.

* * * * *